(12) United States Patent  
Ball

(10) Patent No.: US 9,295,425 B2  
(45) Date of Patent: Mar. 29, 2016

(54) TRANSDUCER FOR STAPEDIUS MONITORING

(75) Inventor: Geoffrey R. Ball, Axams (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 0 days.

(21) Appl. No.: 13/086,841

(22) Filed: Apr. 14, 2011

(65) Prior Publication Data

US 2011/0255731 A1  Oct. 20, 2011

Related U.S. Application Data

(60) Provisional application No. 61/324,574, filed on Apr. 15, 2010.

(51) Int. Cl.
*H04R 1/00* (2006.01)
*A61B 5/00* (2006.01)
(Continued)

(52) U.S. Cl.
CPC ............... *A61B 5/6817* (2013.01); *A61B 5/11* (2013.01); *A61B 5/12* (2013.01); *B06B 1/045* (2013.01); *G01H 11/02* (2013.01); *H04R 11/04* (2013.01); *H04R 25/606* (2013.01); *A61B 5/121* (2013.01);
(Continued)

(58) Field of Classification Search
CPC .......... A61B 5/6817; A61B 5/12; A61B 5/11; A61B 2562/0223; A61B 5/121; A61B 1/227; A61B 2560/045; A61B 2560/0443; B06B 1/045; H04R 25/606; H04R 11/04; H04R 2209/041; G01H 11/02

USPC .......... 381/396, 312, 60, 320, 328, 23.1, 190, 381/191; 181/126, 135, 130; 600/25, 300, 600/559, 379, 459, 546; 73/585, 645, 649, 73/662, 576, 587, 10, 570; 335/213, 205
See application file for complete search history.

(56) References Cited

U.S. PATENT DOCUMENTS 3,101,422 A * 8/1963 Church et al. ................ 310/26  
3,487,403 A   12/1969 Phil (Continued)

FOREIGN PATENT DOCUMENTS

EP    2 031 896 A2   3/2009   ............ H04R 25/00  
GB       1094070     12/1967

(Continued)

OTHER PUBLICATIONS

Hobbs, Md, Ph.D., et al., "Magnetic Resonance Image—Guided Proteoics of Human Glioblastoma Multiforme," *Journal of Magnetic Resonance Imaging*, pp. 530-536, 2003.

(Continued)

*Primary Examiner* — Davetta W Goins  
*Assistant Examiner* — Oyesola C Ojo  
(74) *Attorney, Agent, or Firm* — Sunstein Kann Murphy & Timbers LLP

(57) ABSTRACT

An electro-magnetic transducer assembly includes a first component. The first component includes at least one magnet, and optionally a first attachment mechanism for attaching the first component to a vibrating structure. A coil assembly includes a second attachment mechanism for removably attaching the coil assembly to the first component. The coil assembly further includes at least one coil that produces a signal representative of the vibration of the at least one magnet. An output port provides the signal.

8 Claims, 12 Drawing Sheets

(51) Int. Cl.

| | | |
|---|---|---|
| A61B 5/11 | (2006.01) | |
| A61B 5/12 | (2006.01) | |
| B06B 1/04 | (2006.01) | |
| G01H 11/02 | (2006.01) | |
| H04R 11/04 | (2006.01) | |
| H04R 25/00 | (2006.01) | |

(52) U.S. Cl.
CPC ... *A61B 2562/0223* (2013.01); *H04R 2209/041* (2013.01)
USPC .......................................... 381/396; 600/25

(56) References Cited

U.S. PATENT DOCUMENTS

| | | | | |
|---|---|---|---|---|
| 3,573,812 | A | 4/1971 | Pihl | 340/373 |
| 3,801,767 | A | 4/1974 | Marks | 200/161 |
| 3,987,967 | A | 10/1976 | Kuznetsov et al. | 241/1 |
| 4,038,990 | A | 8/1977 | Thompson | 128/419 PG |
| 4,199,741 | A | 4/1980 | Serrus Paulet | 335/206 |
| 4,257,936 | A | 3/1981 | Matsumoto et al. | 524/413 |
| 4,317,969 | A | 3/1982 | Riegler et al. | 200/52 R |
| 4,596,971 | A | 6/1986 | Hirabayashi et al. | 335/205 |
| 4,628,907 | A | 12/1986 | Epley | 128/1.6 |
| 4,785,816 | A | 11/1988 | Dow et al. | 600/446 |
| RE32,947 | E | 6/1989 | Dormer et al. | 128/420.6 |
| 4,868,530 | A | 9/1989 | Ahs | 335/207 |
| 4,918,745 | A | 4/1990 | Hutchison | 455/41 |
| 5,015,224 | A | 5/1991 | Maniglia | 600/25 |
| 5,183,056 | A | 2/1993 | Dalen et al. | 128/782 |
| 5,434,549 | A | 7/1995 | Hirabayashi et al. | 335/229 |
| 5,456,654 | A | 10/1995 | Ball | 600/25 |
| 5,538,219 | A | 7/1996 | Osterbrink | 251/129.15 |
| 5,554,096 | A | 9/1996 | Ball | 600/25 |
| 5,624,376 | A | 4/1997 | Ball et al. | 600/25 |
| 5,630,835 | A | 5/1997 | Brownlee | 607/60 |
| 5,716,407 | A | 2/1998 | Knapp et al. | 623/11 |
| 5,724,014 | A | 3/1998 | Leikus et al. | 335/4 |
| 5,749,912 | A | 5/1998 | Zhang et al. | 607/57 |
| 5,800,336 | A | 9/1998 | Ball et al. | 600/25 |
| 5,842,967 | A * | 12/1998 | Kroll | 600/25 |
| 5,857,958 | A | 1/1999 | Ball et al. | 600/25 |
| 5,877,664 | A | 3/1999 | Jackson, Jr. | 335/205 |
| 5,897,486 | A | 4/1999 | Ball et al. | 600/25 |
| 5,913,815 | A | 6/1999 | Ball et al. | 600/25 |
| 6,040,762 | A | 3/2000 | Tompkins | 340/426.24 |
| 6,175,767 | B1 | 1/2001 | Doyle, Sr. | 607/57 |
| 6,178,079 | B1 | 1/2001 | Renger | 361/118 |
| 6,178,353 | B1 | 1/2001 | Griffith et al. | 607/61 |
| 6,190,305 | B1 | 2/2001 | Ball et al. | 600/25 |
| 6,208,235 | B1 | 3/2001 | Trontelj | 340/10.1 |
| 6,208,882 | B1 * | 3/2001 | Lenarz et al. | 600/379 |
| 6,217,508 | B1 | 4/2001 | Ball et al. | 600/25 |
| 6,219,580 | B1 | 4/2001 | Faltys et al. | 607/57 |
| 6,291,901 | B1 * | 9/2001 | Cefo | B60L 8/00 290/1 R |
| 6,292,678 | B1 | 9/2001 | Hall et al. | 600/374 |
| 6,295,472 | B1 | 9/2001 | Rubinstein et al. | 607/55 |
| 6,313,551 | B1 | 11/2001 | Hazelton | 310/12 |
| 6,348,070 | B1 | 2/2002 | Teissi et al. | 623/11.11 |
| 6,358,281 | B1 | 3/2002 | Berrang et al. | 623/10 |
| 6,475,134 | B1 | 11/2002 | Ball et al. | 600/25 |
| 6,505,062 | B1 | 1/2003 | Ritter et al. | 600/407 |
| 6,506,987 | B1 | 1/2003 | Woods | 290/61.62 |
| 6,522,909 | B1 | 2/2003 | Garibaldi et al. | 600/424 |
| 7,054,691 | B1 * | 5/2006 | Kuzma et al. | 607/57 |
| 7,642,887 | B2 * | 1/2010 | Zimmerling | 335/296 |
| 8,340,335 | B1 * | 12/2012 | Shennib | H04R 25/60 381/315 |
| 2005/0027332 | A1 * | 2/2005 | Avrahami et al. | 607/61 |
| 2005/0033384 | A1 | 2/2005 | Sacha | 607/57 |
| 2005/0148814 | A1 * | 7/2005 | Fischi et al. | 600/37 |
| 2006/0244560 | A1 | 11/2006 | Zimmerling et al. | 335/207 |
| 2007/0126540 | A1 * | 6/2007 | Zimmerling | B06B 1/045 335/205 |
| 2009/0299215 | A1 | 12/2009 | Zhang | |
| 2010/0004716 | A1 | 1/2010 | Zimmerling et al. | 607/57 |
| 2011/0046432 | A1 * | 2/2011 | Simon et al. | 600/14 |

FOREIGN PATENT DOCUMENTS

| | | | | |
|---|---|---|---|---|
| GB | 1468890 | | 3/1977 | B26D 5/00 |
| JP | 2004023821 | | 1/2004 | H02K 7/09 |
| SU | 1690749 | | 11/1991 | A61F 11/04 |
| WO | WO 97/32629 | A1 | 9/1997 | A61N 1/32 |
| WO | WO 00/10361 | A2 | 2/2000 | |
| WO | WO 03/036560 | A2 | 5/2003 | G06K 11/18 |
| WO | WO 03/081976 | A2 | 10/2003 | |
| WO | WO 03/092326 | A1 | 11/2003 | H04R 25/00 |
| WO | WO 2004/114723 | A2 | 12/2004 | H04R 25/00 |
| WO | 2009/111802 | A1 | 9/2009 | |
| WO | WO 2011/130490 | | 10/2011 | H04R 9/02 |

OTHER PUBLICATIONS

Teissl, et al., "Magnetic Resonance Imaging and Cochlear Implants Compatibility and Safety Aspects," *Journal of Magnetic Resonance Imaging*, vol. 9, pp. 26-38, Jan. 1999.

International Searching Authority, International Search Report—International Application No. PCT/IB2004/002588 dated Feb. 23, 2005, together with the Written Opinion of the International Searching Authority, 17 pages.

International Searching Authority, International Search Report, dated Nov. 28, 2003, PCT/IB03/02283, 7 pages.

Heller, et al., "Evaluation of MRI Compatibility of the Modified Nucleus Multichannel Auditory Brainstem and Cochlear Implants," *The American J. of Otology*, 17(5), pp. 724-729, Sep. 1996.

Teissl, et al., "Cochlear Implants: In Vitro Investigation of Electromagnetic Interference at MR Imaging—Compatibility and Safety Aspects," *Radiology*, 208(3), pp. 700-708. Sep. 1998.

United States Patent and Trademark Office, Office Action dated Feb. 12, 2007, pertaining to U.S. Appl. No. 11/158,322, 6 pages.

Bromberg & Sunstein LLP, Response filed May 14, 2007, to Office Action dated Feb. 12, 2007, pertaining to U.S. Appl. No. 11/158,322, 14 pages.

United States Patent and Trademark Office, Office Action dated Mar. 17, 2008, pertaining to U.S. Appl. No. 11/158,322, 20 pages.

Bromberg & Sunstein LLP, Response filed Jun. 17, 2008 to Office Action dated Mar. 17, 2008, pertaining to U.S. Appl. No. 11/158,322, 10 pages.

United States Patent and Trademark Office, Office Action dated Jan. 14, 2008, pertaining to U.S. Appl. No. 11/475,705, 8 pages.

Bromberg & Sunstein LLP, Response filed Jun. 13, 2008 to Office Action dated Jan. 14, 2008, pertaining to U.S. Appl. No. 11/475,705, 10 pages.

United States Patent and Trademark Office, Final Office Action dated Nov. 4, 2008, pertaining to U.S. Appl. No. 11/475,705, 10 pages.

European Patent Office, European Search Report—European Application No. 08075886.5, dated Jun. 3, 2009, 8 pages.

Bromberg & Sunstein LLP, Office Action dated Jun. 4, 2007, pertaining to U.S. Appl. No. 11/671,132, 11 pages.

Bromberg & Sunstein LLP, Final Office Action dated May 7, 2009, pertaining to U.S. Appl. No. 11/671,132, 9 pages.

Bromberg & Sunstein LLP, Office Action dated Oct. 27, 2008, pertaining to U.S. Appl. No. 11/671,132, 7 pages.

Bromberg & Sunstein LLP, Final Office Action dated Jun. 26, 2008, pertaining to U.S. Appl. No. 11/671,132, 11 pages.

Bromberg & Sunstein LLP, Response to Office Action of Jun. 4, 2007, pertaining to U.S. Appl. No. 11/671,132, dated Nov. 26, 2007, 11 pages.

Bromberg & Sunstein LLP, Response to Office Action of Oct. 27, 2008, pertaining to U.S. Appl. No. 11/671,132, dated Jan. 5, 2009, 13 pages.

Bromberg & Sunstein LLP, Response to Office Action of Jun. 26, 2008, pertaining to U.S. Appl. No. 11/671,132, dated Sep. 19, 2008, 8 pages.

(56) References Cited

OTHER PUBLICATIONS

Sunstein Kann Murphy & Timbers LLP, Request for Continued Examination and Response to Office Action of May 7, 2009, pertaining to U.S. Appl. No. 11/671,132, dated Jul. 29, 2009, 15 pages.

International Searching Authority, International Search Report—International Application No. PCT/US2011/032453, dated Oct. 13, 2011, together with the Written Opinion of the International Searching Authority, 8 pages.

European Patent Office, Extended European Search Report—International Application No. 11769572.6-1657, Jun. 5, 2014, 7 pages.

* cited by examiner

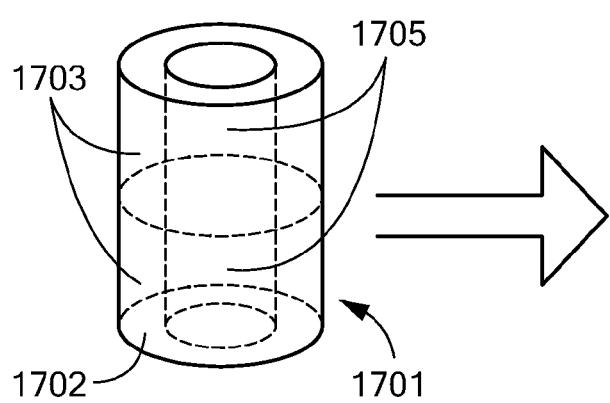
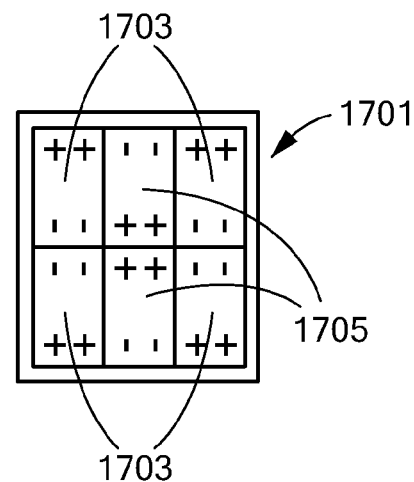
FIG. 17A
FIG. 17B
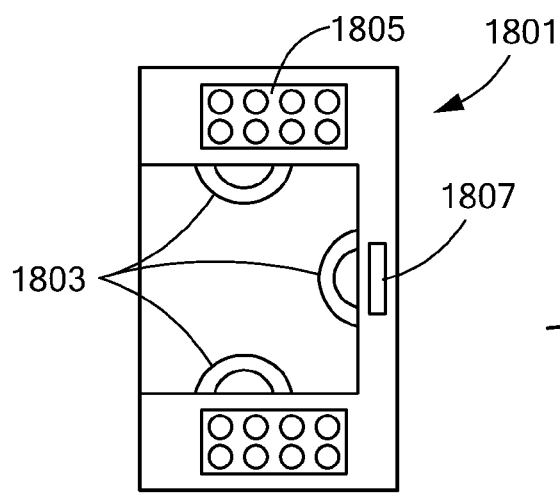
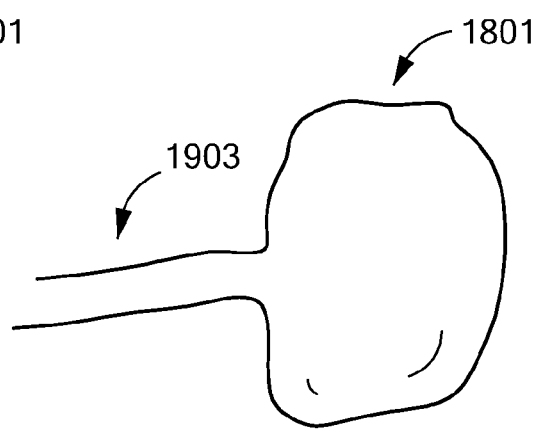
FIG. 18
FIG. 19

TRANSDUCER FOR STAPEDIUS MONITORING

CROSS REFERENCE TO RELATED APPLICATIONS

This application claims priority from U.S. provisional patent application Ser. No. 61/324,574 filed Apr. 15, 2010, entitled "Transducer for Stapedius Monitoring," which is hereby incorporated herein by reference in its entirety.

The present application is related to U.S. patent application Ser. No. 12/348,570, entitled "System and Method for Reducing the Effect of Magnetic Fields on an Implanted Electro-Magnetic Transducer," filed Jan. 5, 2009, which claims priority from U.S. provisional application Ser. No. 61/019,352, filed Jan. 7, 2008. U.S. patent application Ser. No. 12/348,570 also is a continuation-in-part of U.S. patent application Ser. No. 11/671,132, entitled "System and Method for Reducing the Effect of Magnetic Fields on an Implanted Electro-Magnetic Transducer," filed Feb. 5, 2007, which in turn is a divisional of U.S. patent application Ser. No. 10/877,510, entitled "System and Method for Reducing Effect of Magnetic Fields on a Magnetic Transducer," filed Jun. 25, 2004, which in turn claims priority from U.S. provisional application Ser. No. 60/482,687, entitled "Reducing Effect of Magnetic Fields on a Magnetic Transducer," filed Jun. 26, 2003. U.S. patent application Ser. No. 10/877,510 is also a continuation-in-part of U.S. patent application Ser. No. 10/405,093, filed Apr. 1, 2003, entitled "Reducing Effects of Magnetic and Electromagnetic Fields on an Implant's Magnet And/Or Electronics," which claims priority from U.S. provisional application number Ser. No. 60/369,208, filed Apr. 1, 2002 and from U.S. provisional application No. 60/387,455, filed Jun. 10, 2002. Each of the above-mentioned applications is hereby incorporated herein by reference.

TECHNICAL FIELD

The present invention relates to transducers and external magnetic fields, and more particularly, to a transducer that can be used, for example, to monitor the stapedius. Various embodiments further reduce the effect of external magnetic fields on the transducer.

BACKGROUND ART

Implants often include various electro-magnetic transducers that may function as an actuator, a sensor, and/or a switch. An example of an implant with an electro-magnetic actuator is a middle ear implant which mechanically drives the ossicular chain. Such a middle ear implant that includes a floating mass transducer was developed by Geoffrey Ball et al., and is shown in FIG. 1 (see U.S. Pat. Nos. 5,913,815; 5,897,486; 5,624,376; 5,554,096; 5,456,654; 5,800,336; 5,857,958; and 6,475,134, each of which is incorporated herein by reference).

As shown in FIG. 1, the floating mass transducer 100 includes a housing 101 and at least one coil 102 and 103 coupled to the housing 101. A magnet 104 disposed within the housing 101 is biased by biasing elements 106. The biasing elements 106 are used in defining a resonance frequency, and also reduce friction between the magnet 104 and the interior surface of the housing 101 that may cause distortion. Electrical signals through the at least one coil 102 and 103 cause the magnet 104 to vibrate relative to the housing 101 along an axis 105. The vibration of the magnet 104 causes inertial vibration of the housing 101, which consequently produces vibrations in the inner ear.

Implants may also include an electro-magnetic sensor. Electro-magnetic sensors may be utilized, without limitation, in a microphone, such as a microphone used in converting the mechanical vibrations of an ossicle in the middle ear into an electrical signal.

Another application of an electro-magnetic sensor may be to detect the stapedius reflex. The stapedius reflex is a reflex in the middle ear typically elicited when exceeding the maximum comfortable loudness level. More, particularly, the tympanic muscle and the so-called stapedius muscle are located in the middle ear. The tympanic muscle is linked to the hammer, the stapedius muscle being connected via a tendon to the stirrup. In case of an excessively high sound pressure, which could damage the inner ear, both muscles contract reflexively, so that the mechanical coupling of the eardrum to the inner ear (and thus also the force transmission) is decreased. In this way, it is possible to protect the inner ear from excessively high sound pressures. This tensing of the stapedius muscle triggered as a result of high sound pressures is also referred to as the stapedius reflex. Medically relevant information about the functional capability of the ear may be obtained from the diagnosis of the stapedius reflex. Furthermore, the measurement of the stapedius reflex is useful for setting and/or calibrating so-called cochlear implants, because the sound energy perceived by a patient may be concluded from the measured stapedius reflex.

Instead of an electro-magnetic sensor, other methods for detection of the stapedius reflex typically require a sophisticated surgical technique and special electrodes for recording the myo-electric evoked response, such as a hook electrode patented by Lenarz et al. (see for example, U.S. Pat. No. 6,208,882), or are inconvenient, such as stapedius reflex detection by external tympanometers. FIG. 2 (prior art) depicts an electro-magnetic sensor which in principle could be employed as a stapedius reflex sensor.

Various problems may arise when an electro-magnetic sensor is used to detect the stapedius reflex. One problem is that measuring the stapedius reflex to calibrate a cochlear implant often is performed over an extended period of time of weeks or more. Thus, the sensor and associated wiring requires repetitious installation and removal from the stapedius.

Additionally, upon a wearer of such an auditory (cochlear or middle ear) prosthesis having to undergo Magnetic Resonance Imaging (MRI) examination, interactions between the implanted electro-magnetic transducer and the applied external MRI magnetic field may, at higher field strength (i.e. above about 1 Tesla), produce three potentially harmful effects:

1. The implanted magnet experiences a torque (T=m×B) that may twist the electro-magnetic transducer out of its position, thereby injuring the implant wearer and/or destroying the mechanical fixation, as shown in FIG. 3 (prior art).

2. Due to the external magnetic field, the implanted magnet becomes partly demagnetized and this may lead to damage or at least to a reduced power efficiency of the electro-magnetic transducer after exposure to the MRI field.

3. Magnetic RF pulses (magnetic field $B_1$ in MRI) emitted by the MR unit can induce voltages in the coil(s) of the electro-magnetic transducer and this may destroy the transducer and/or may harm the patient.

Because of these risks it may be generally forbidden to undergo (at least high-field) MRI examination for patients with an implant with electro-magnetic transducer. This may exclude the patient from certain important diagnosis methods.

SUMMARY OF THE INVENTION

In accordance with an embodiment of the invention, an electro-magnetic transducer assembly includes a first component. The first component includes at least one magnet. A coil assembly includes a second attachment mechanism for removably attaching the coil assembly to the first component. The coil assembly further includes at least one coil that produces a signal representative of the vibration of the at least one magnet. An output port provides the signal.

In accordance with related embodiments of the invention, the transducer assembly may further include a first attachment mechanism for attaching the first component to a vibrating structure. The first attachment mechanism may be for attaching to a structure of the ear, such as a stapedius of a patient. The first attachment mechanism may include a zip tie. The second attachment mechanism may include a male shaped housing associated with the first component, and a female shaped housing associated with the coil assembly, such that the male shaped housing is inserted into the female shaped housing to operatively connect the first component to the coil assembly.

In accordance with further related embodiments of the invention, the at least one magnet may include a plurality of magnets arranged in an anti-parallel configuration. Each magnet may be capable of turning in any direction within the housing, wherein translational movement of each magnet is substantially restricted to movement along a single axis, and wherein vibration of the housing causes vibration of the at least one magnet. At least one magnet may be substantially spherical. The coil assembly may further include at least one spring for damping vibration of the at least one magnet.

In accordance with another embodiment of the invention, a method for measuring a vibration of a structure includes removably attaching a first component to the structure, the first component including at least one magnet. A coil assembly is attached to the first component, the coil assembly for producing a signal representative of the vibration of the at least one magnet. The signal is provided to an output port of the coil assembly. The coil assembly is removed from the first component, leaving the first component attached to the structure.

In accordance with related embodiments of the invention, the structure may be associated with the ear of a patient, such as a stapedius of a patient. The at least one magnet may include a plurality of magnets arranged in an anti-parallel configuration. Each magnet may be capable of turning in any direction within the housing, wherein translational movement of each magnet is substantially restricted to movement along a single axis, and wherein vibration of the housing causes vibration of the at least one magnet. The at least one magnet may be substantially spherical. The vibration of the at least one magnet may be damped.

In accordance with further related embodiments of the invention, a male shaped housing may be associated with the first component, and a female shaped housing associated with the coil assembly, such that attaching the coil assembly to the first component includes inserted the male shaped housing into the female shaped housing. The method may further include programming a hearing implant based, at least in part, on the signal.

BRIEF DESCRIPTION OF THE DRAWINGS

The foregoing features of the invention will be more readily understood by reference to the following detailed description, taken with reference to the accompanying drawings, in which:

FIGS. 17(a) and 17(b) schematically show a first component of the electromagnetic transducer, in accordance with one embodiment of the invention.

FIG. 18 schematically shows a coil assembly of the electromagnetic transducer, in accordance with an embodiment of the invention.

FIGS. 19 and 20 show varying views of the coil assembly 1801, in accordance with one embodiment of the invention.

DETAILED DESCRIPTION OF SPECIFIC EMBODIMENTS

In illustrative embodiments, a coil and associated wiring is removably attached to a transducer, allowing for removal of the coil and wiring from the transducer when the transducer is not in use. This can be advantageous, for example, when measuring the stapedius reflex to calibrate a cochlear implant. This measurement is often performed over an extended period of time. As opposed to repetitious installation and removal from the stapedius, a portion of the transducer can remain installed on the stapedious when testing is not being performed. In further embodiments, the transducer may advantageously reduce the effect of external magnetic fields, so that, for example, the transducer is safe against induction of voltages arising from magnetic pulses that may occur, for example, during Magnetic Resonance Imaging (MRI). Details are described below.

Figure 1:
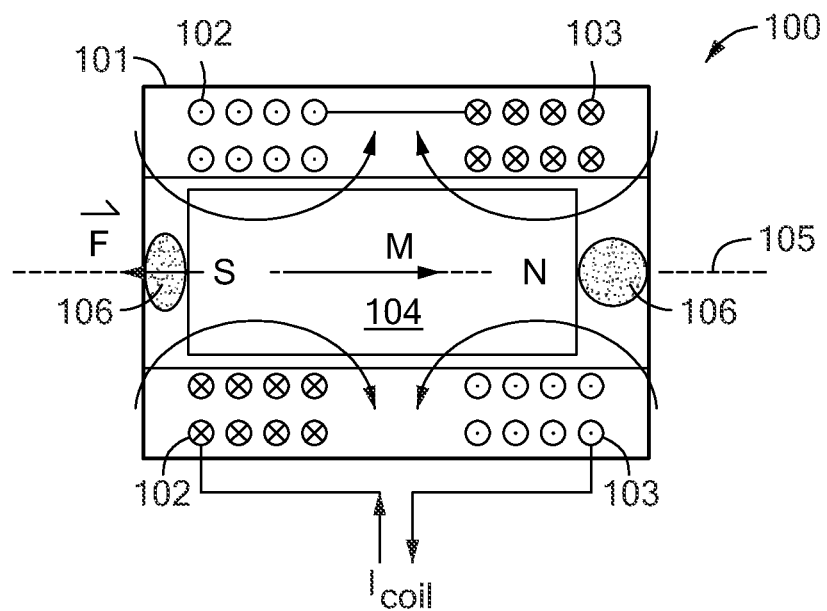
FIG. 1 schematically shows an electro-magnetic transducer with differential coils and a cylindrical magnet acting as a mechanical stimulator, as employed in a middle ear implant, where a current flow in the coils results in a movement of the magnet which translates into a movement of the housing (PRIOR ART)
Figure 2:
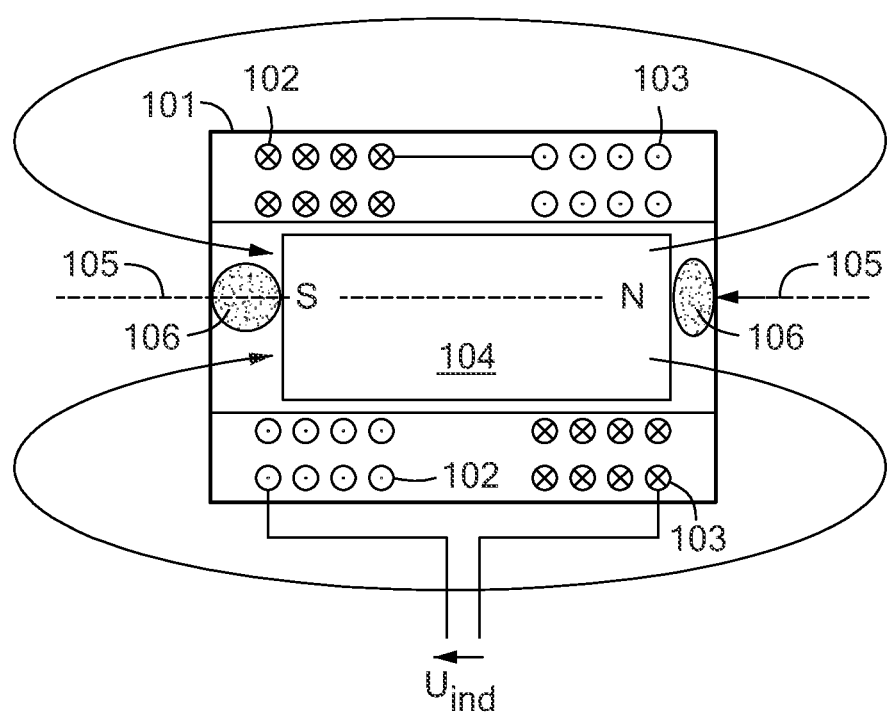
FIG. 2 schematically shows an electro-magnetic transducer with differential coils and a cylindrical magnet acting as a mechanical sensor, where the movement of the housing translates into a movement of the magnet, resulting in an induction of voltages in the coils (PRIOR ART)
Figure 3:
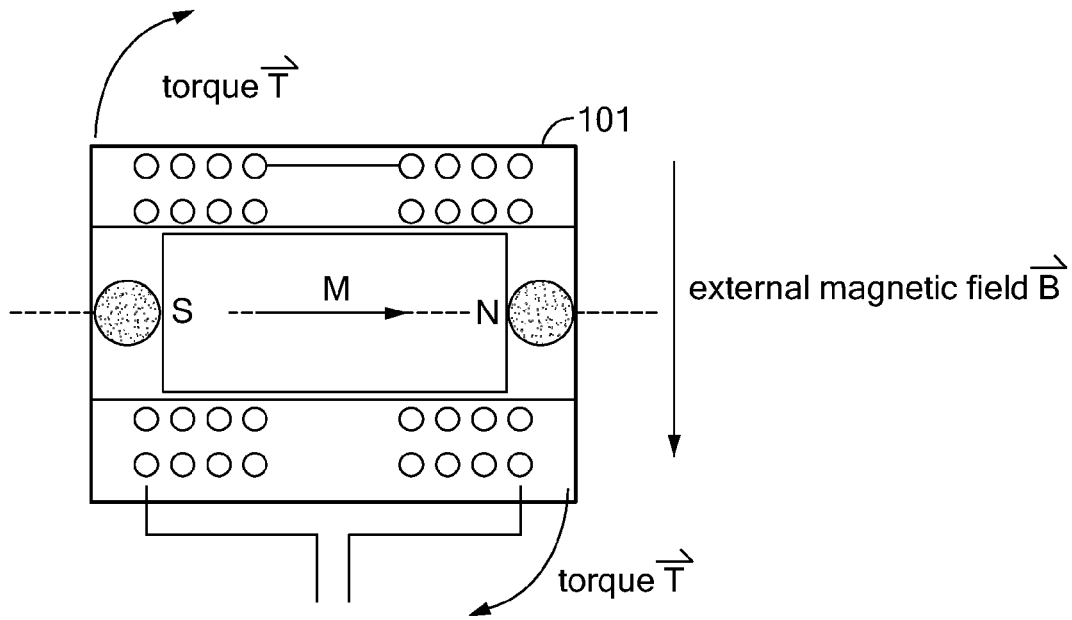
FIG. 3 schematically shows an electro-magnetic transducer experiencing a torque as a result of an external magnetic field (e.g. in an MRI scanner) that is not parallel to the magnetic moment of the magnet of the transducer (PRIOR ART)
Figure 4:
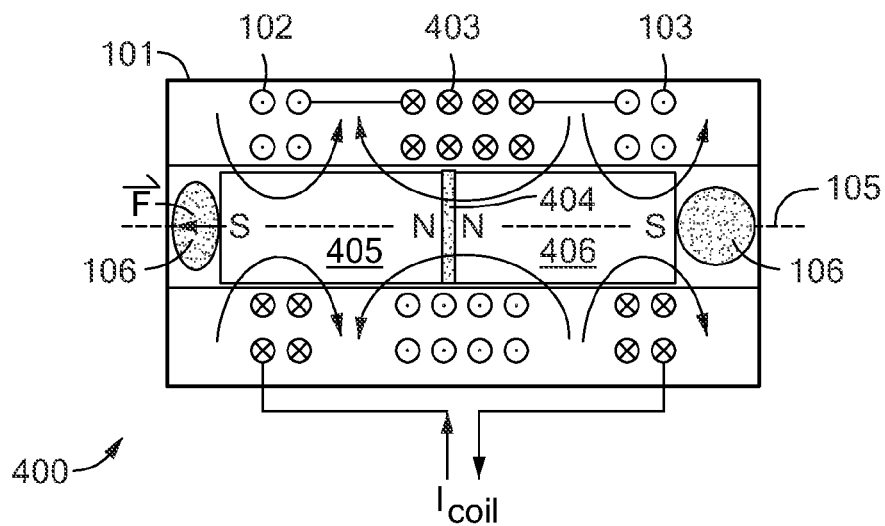
FIG. 4 schematically shows an electro-magnetic transducer acting as a mechanical stimulator, the transducer including two anti-parallel mounted cylindrical magnets and one or more coils, in accordance with one embodiment of the invention.

FIG. 4 shows a transducer 400 acting as a mechanical stimulator in accordance with one embodiment of the invention. As used in this description, and the accompanying claims, the term "transducer" as used herein shall mean a device that converts energy or information of one physical quantity into another physical quantity. A transducer may act as a sensor and/or a stimulator/driver, as known in the art.

The transducer 400 includes a housing 101, which in preferred embodiment is non-ferromagnetic. The housing may be hermetically sealed so as to prevent corrosion and/or leakage of material into or out of the housing. The housing may be made of a biocompatible material, particularly when the transducer is to be implanted. Material used for the housing may include, without limitation, stainless steel, titanium, iron, aluminum, platinum, nylon or a ceramic.

At least one coil 102, 103 and 403 is associated with the housing 101, and may be mounted externally or within the housing 101. For example, as shown in FIG. 4, the housing 101 may be associated with three coils 102, 103, and 403, with the middle coil 403 wound in a direction that is different from the other two coils 102 and 103.

At least two magnets 405 and 406, that may be, without limitation, substantially identical in terms of their magnetic moments and cylindrical in nature, are mounted back to back (for, example, with either their north poles or south poles adjacent) in an anti-parallel configuration along an axis 105 within the housing 401. Since the two magnets 405 and 406 have opposite magnetic moments, the total torque exerted to the arrangement in the presence of an external magnetic field of any orientation (e.g. in an MRI unit) is substantially zero.

Figure 5:
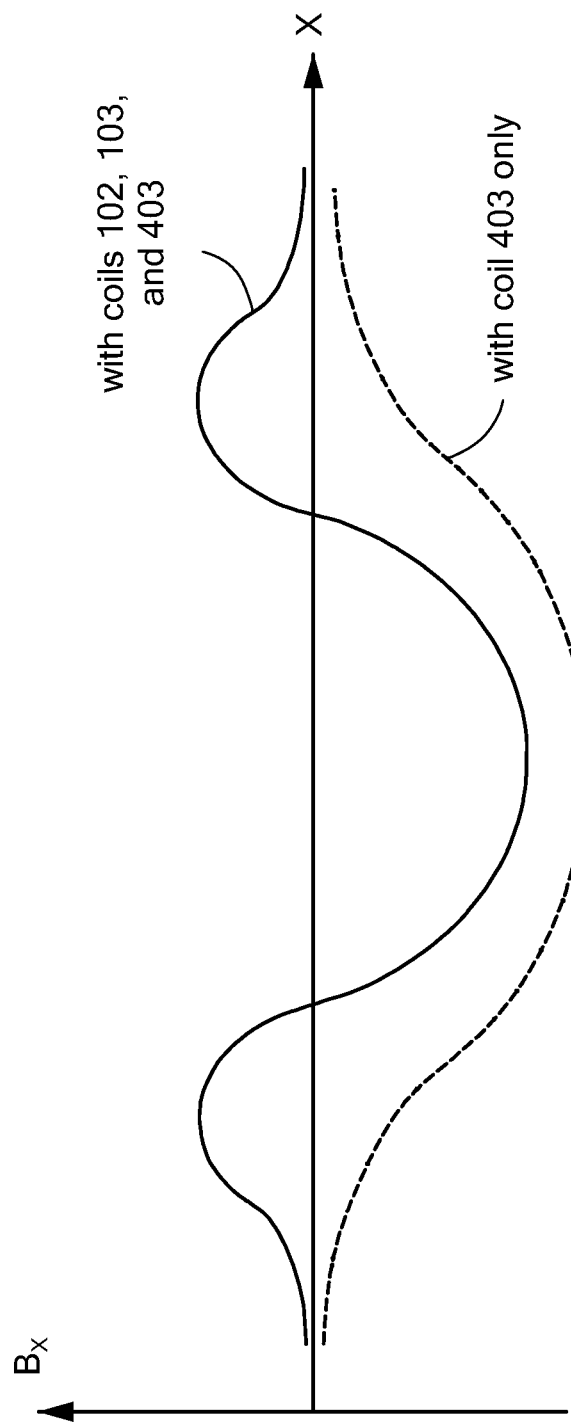
FIG. 5 is a chart illustrating the axial component of the magnetic field generated by a current flow through the coils (and, for comparison, for a current flow only through the inner coil) of the transducer depicted in FIG. 4, in accordance with one embodiment of the invention.

In various embodiments, a simplified arrangement with only one coil may be used. Such an arrangement may be less efficient since the force on the transducer magnets 405 and 406 is proportional to the local gradient of the magnetic field generated by the coil(s) 101, 102 and 403. FIG. 5 shows the axial distribution of the axial component of the magnetic field generated by one and three coils, in accordance with an embodiment of the invention.

Note that the embodiment shown in FIG. 4 works fine for external magnetic field strengths that cannot weaken one of the magnets 405 and 406. At even stronger external magnetic fields, the magnet that is oriented anti-parallel to the external magnetic field may be diminished. This leads to a residual net magnetization for the two magnets 405 and 406, thus resulting in a torque exerted to the two magnets 405 and 406.

In preferred embodiments, the coils 102, 103 and 403 may be arranged such that the net voltage induced from a magnetic RF pulse is substantially zero. For example, in the embodiment shown in FIG. 4, the added inductance of coils 102 and 103 can be chosen to be substantially identical to the inductance of coil 403. Consequently, the induced voltage from coils 102 and 103 will be substantially equal to, and compensate for, the induced voltage from coil 403. This results in the substantial elimination of residual signals produced when the system is exposed to a homogeneous electromagnetic field, such as from an MRI unit.

Figure 6A:
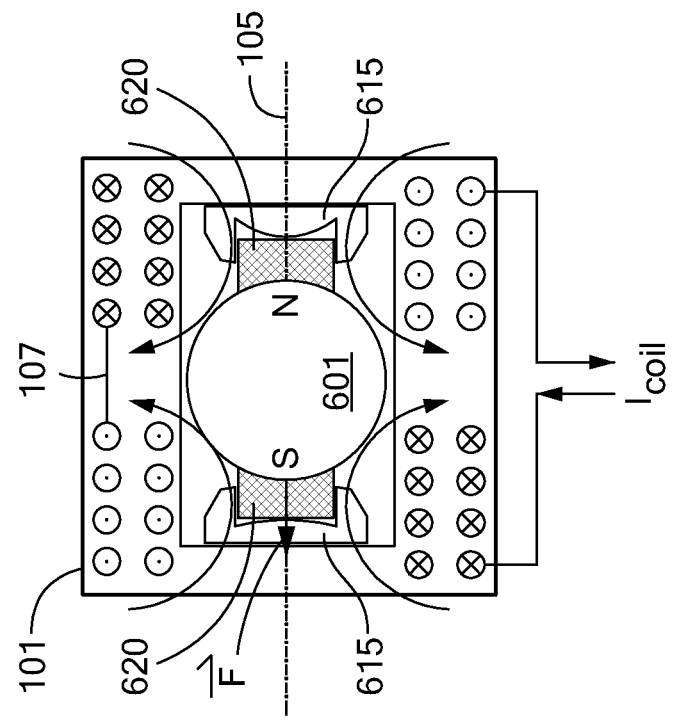
FIG. 6A schematically shows an electro-magnetic transducer acting as a mechanical stimulator, that includes a spherical magnet and a keeper, in accordance with one embodiment of the invention.

FIG. 6A schematically shows a transducer 600 acting as a mechanical stimulator, in accordance with another embodiment of the invention. The transducer 600 includes a housing 101, which is preferably non-ferromagnetic, and which may be hermetically sealed and biocompatible, as described in above embodiments. The transducer 600 further includes a spherical magnet 601, a magnetically soft element 603 (referred to herein and in the claims as a keeper), and at least one coil 102 and 103.

The keeper 603 includes magnetically soft material that becomes magnetized in the direction of an external magnetic field. The keeper 603 may include, without limitation, a solid alloy, Ferrite, or Ferrofluid. When placed adjacent an external part that includes a magnet 601, the keeper 603 becomes magnetized and becomes attracted to the magnet 601, holding/keeping the magnet 601 in place, so that the magnet 601 is prevented from rattling.

The spherical magnet 601 is substantially restricted to movement along the transducer's axis 105 of rotational symmetry, and additionally, is mechanically free to turn in any direction. In the absence of an external magnetic field, an attractive force between the keeper 603 (which is mechanically free to move along the transducer's axis 105 of rotational symmetry) and a magnetic pole of the spherical magnet 601 causes opposing magnetic poles of the magnet 601 to be aligned parallel to the transducer's axis 105 of rotational symmetry. Thus, the spherical magnet 601 can act like a standard cylindrical magnet in a state-of-the-art electro-magnetic transducer. Without the keeper 603, the orientation of the magnetic moment of the spherical magnet 601 would be undefined, and this would lead to an undefined movement of the magnet 601 in the transducer 600. The keeper 603 is held in place by a non-magnetic adapter 602. Alternatively, the non-magnetic adapter 602 may not be needed if the keeper 1202 itself is shaped so as to maintain itself centered on the axis 105. In further embodiments, the keeper 603 may be replaced by any other system or principle that keeps the magnetic moment of the spherical magnet parallel to the axis 105.

In the presence of a strong external magnetic field, the magnetization of the keeper 603 aligns in the direction of the external magnetic field, while the spherical magnet 601 turns to align its magnetic momentum vector with the external magnetic field. Thus, the electro-magnetic transducer 600 is free of torque and cannot be demagnetized in the presence of a strong external magnetic field of any direction and orientation, e.g. during Magnetic Resonance Imaging (MRI). In various embodiments, the two coils 102 and 103 are identical but are winded in opposite directions, ensuring the net voltage induced from a magnetic RF pulse is substantially zero.

Figure 6B:
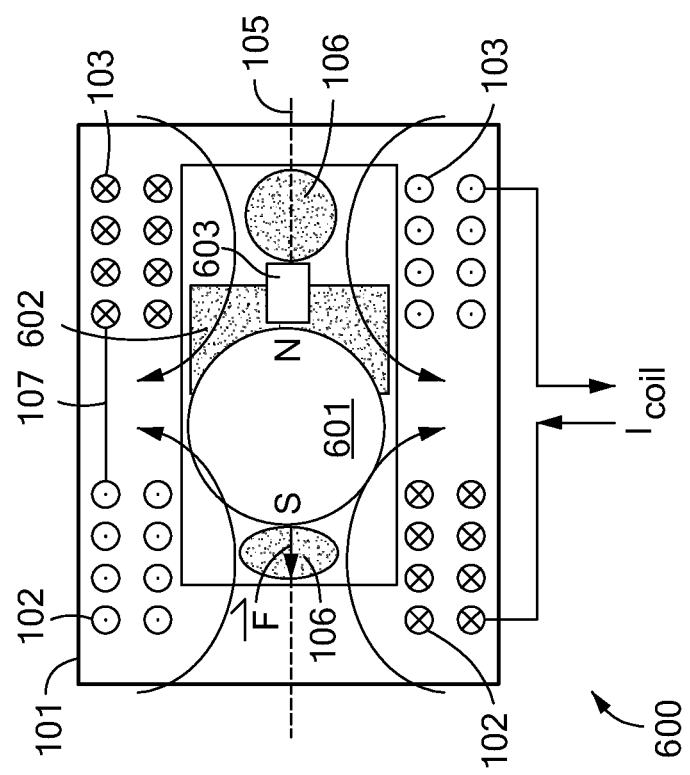
FIG. 6B schematically shows an electro-magnetic transducer acting as a mechanical stimulator, that includes a spherical magnet and two keepers, in accordance with one embodiment of the invention.

FIG. 6B schematically shows an electro-magnetic transducer acting as a mechanical stimulator, which includes a spherical magnet 601 and two keepers 620, in accordance with an embodiment of the invention. Only one spherical magnet 601 is utilized, as the two magnetically soft keepers 620 attract the magnetic poles of the magnet 601 and thus keep the magnet 601 aligned with the axis of symmetry 105. The use of two magnetically-soft keepers instead of only one keeper as shown in the embodiment of FIG. 6A provides increased ability to keep the magnetic axis of the spherical magnet parallel to the axis of the transducer's axis 105 of rotational symmetry.

In various embodiments, the two magnetically soft keepers 620 are held by two biasing members 615. Biasing members 615 are typically non-magnetic and may be, without limitation, elastic, resilient and/or flexible. For example, the two biasing members 615 may be fixation springs, which hold the keepers 620 along the axis of symmetry 105 and (with its elastic middle part) elastically take up axial forces of the keepers 620. Since the keepers 620 magnetically attract the spherical magnet 601, the fixation springs may hold the spherical magnet 601 in place such that it does not come in direct contact with, or has minimal contact with, the inner wall of the housing 101. In various embodiments, biasing elements 615 may not need to hold keepers 620 in place, as keepers 620 may be shaped so as to maintain themselves centered on the axis 105, or each keeper may be held in place in a manner similar to FIG. 6(a). In further embodiments, the keepers 620 may be replaced by any other system or principle that keeps the magnetic moment of the spherical magnet parallel to the axis 105 of symmetry of the transducer.

An alternating current flow through the two coils 102 and 103, which are differently oriented and which are electrically connected by a wire 107 causes the spherical magnet 601 moving back and forth (i.e. it vibrates along the axis of symmetry), pushing the keepers 620 alternately towards the left and towards the right fixation springs, which in turn cause a vibration of the transducer. The embodiment of FIG. 6B advantageously has a short overall length compared to, for example, embodiments with two spherical magnets (e.g. see FIG. 7, described in more detail below). Additionally, the embodiment of FIG. 6B advantageously has a symmetric design. Advantages of a symmetric design include easier production, as the same components are on both sides of magnet. Also, a symmetric design helps ensure a symmetric vibrational response in both directions. This is the case also when operating the device in reverse mode (i.e. as a vibration sensor). Such symmetric embodiments advantageously may also result in reduced harmonic distortions which might occur in an un-symmetric design.

Figure 7:
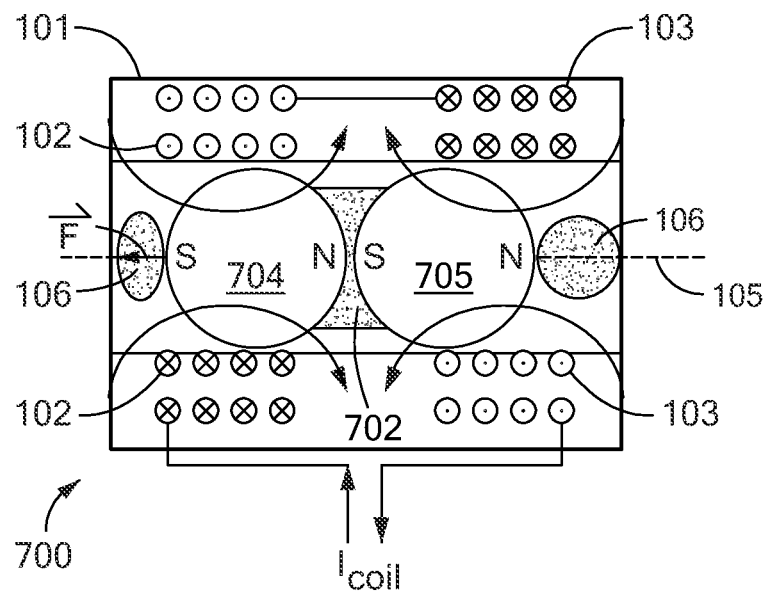
FIG. 7 schematically shows an electro-magnetic transducer acting as a mechanical stimulator, the transducer including two spherical magnets and a keeper, in accordance with one embodiment of the invention.
Figure 8:
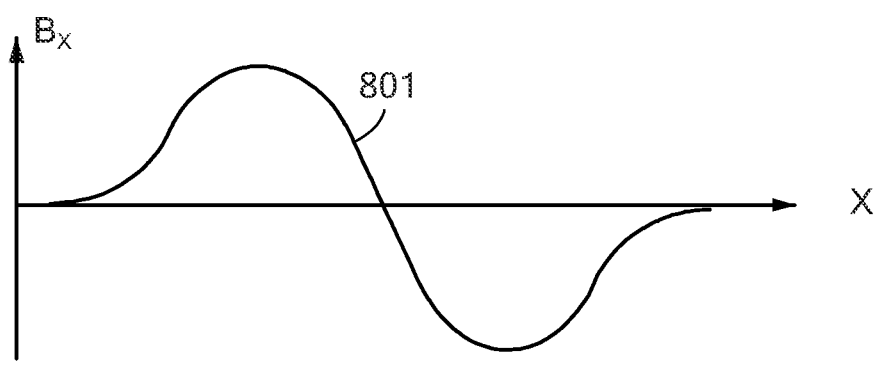
FIG. 8 is a chart illustrating the axial component of the magnetic field generated by a current flow through the coils of the transducer depicted in FIG. 7, in accordance with one embodiment of the invention.

In accordance with another embodiment of the invention, there is provided a transducer 700 acting as a mechanical stimulator that includes a housing 101 with at least two coils 102, 103 and at least two spherical magnets 704, 705, as shown in FIG. 7. The spherical magnets 704 and 705 are mechanically free to turn in any direction and to move along the device's axis 105 of rotational symmetry. The housing 101 may have a cylindrical arrangement and be non-ferromagnetic, similar to above described embodiments. The axial magnetic field distribution 801 generated by the coils is depicted in FIG. 8.

A non-magnetic adapter 702 with spherical calottes, preferably made of or coated by Teflon® or a similar material, may be placed between the two attracting spherical magnets 704 and 705 to reduce the punctual pressure and, when the spheres turn, the friction between the two spheres 704 and 705. Furthermore, the adapter 702 may include a material that reduces the reluctance between the magnets 704 and 705.

In the absence of any strong external magnetic field, the spherical magnets 704 and 705 are magnetically attracted together (the north pole of one magnet is attracted by the south pole of the other magnet) and form a stable magnetic moment with undefined orientation parallel to the axis 105 of symmetry. Since the attractive force between the spheres 704 and 705 is designed to be much stronger than the force resulting from the magnetic field generated by the coils 102, 103, the orientation of the magnetic moment of the magnets 704 and 705 can generally not be altered by a current in the coils 102, 103. The spherical magnets 704 and 705 thus act like a single standard (cylindrically shaped) magnet in a state-of-the-art electro-magnetic transducer, where the magnet can only move along its axis but cannot change its orientation.

Figure 10:
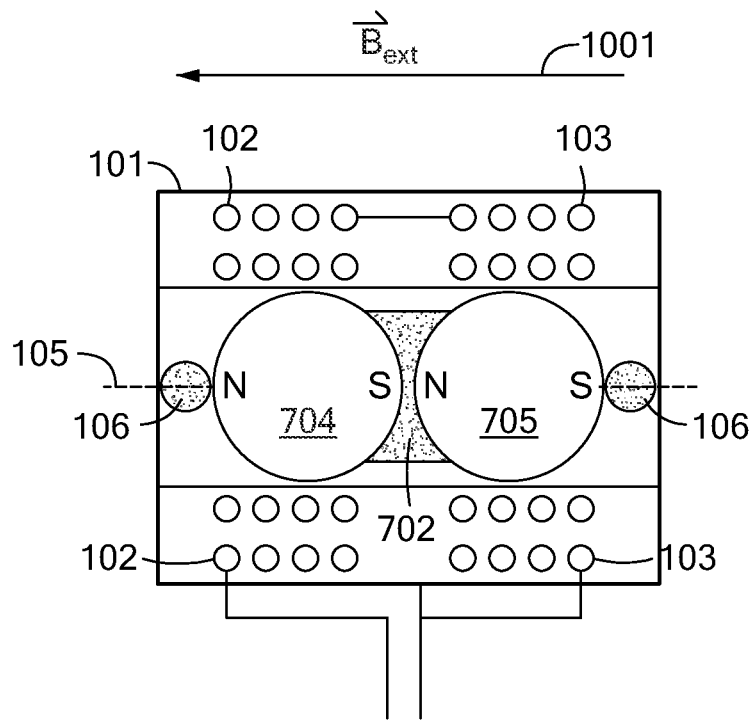
FIG. 10 schematically shows the embodiment of FIG. 7 when a strong external magnetic field (e.g. of an MR scanner) oriented anti-parallel to the magnetic moments of the spherical magnets is present, the spheres rotating by 180° to align their magnetic field with the external field, in accordance with one embodiment of the invention.
Figure 11:
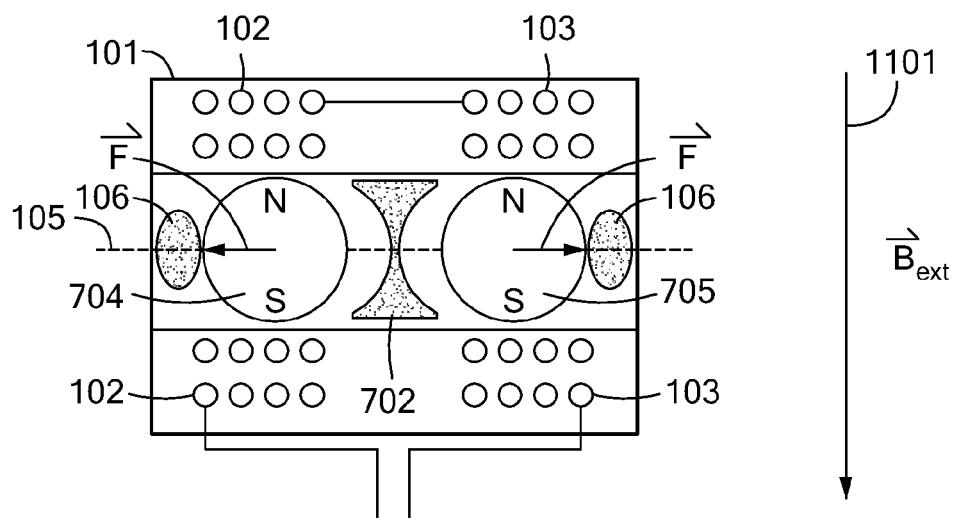
FIG. 11 schematically shows the embodiment of FIG. 7 when a strong external magnetic field (e.g. of an MR scanner) oriented perpendicular to the magnetic moments of the spherical magnets is present, the spheres rotating by 90° to align their magnetic field with the external field, with the spherical magnets repelling each other, in accordance with one embodiment of the invention.

When a strong external magnetic field of any direction and orientation is present, the spherical magnets 704 and 705 can align their magnetic moments with that external field. If the external field is orientated parallel to the device's axis 105 of symmetry and is facing into the same direction like the magnetic moments of the spherical magnets 704 and 705, the magnets 704 and 705 keep their orientation. In case of an anti-parallel external magnetic field 1001, the two spheres 704 and 705 (and the direction of their magnetic moment) flip by 180°, as shown in FIG. 10. The two spherical magnets 704 and 705 of the electro-magnetic transducer act like a single magnet with reverse magnetic poles, causing a movement of the magnets 704 and 705 into the opposite direction. If an external magnetic field 1101 is oriented normal to the device's axis 105 of rotational symmetry, the spherical magnets 704 and 705, when aligning their magnetic moments parallel to the orientation of the external field, are repelling each other, but like for any orientation of the external magnetic field no torque is exerted to the magnets, and no (partial) demagnetization of the magnets 704 and 705 can occur, as shown in FIG. 11. Because the two coils 102 and 103 are identical but winded in different orientation, the net voltage induced from a magnetic RF pulse is zero.

Figure 14:
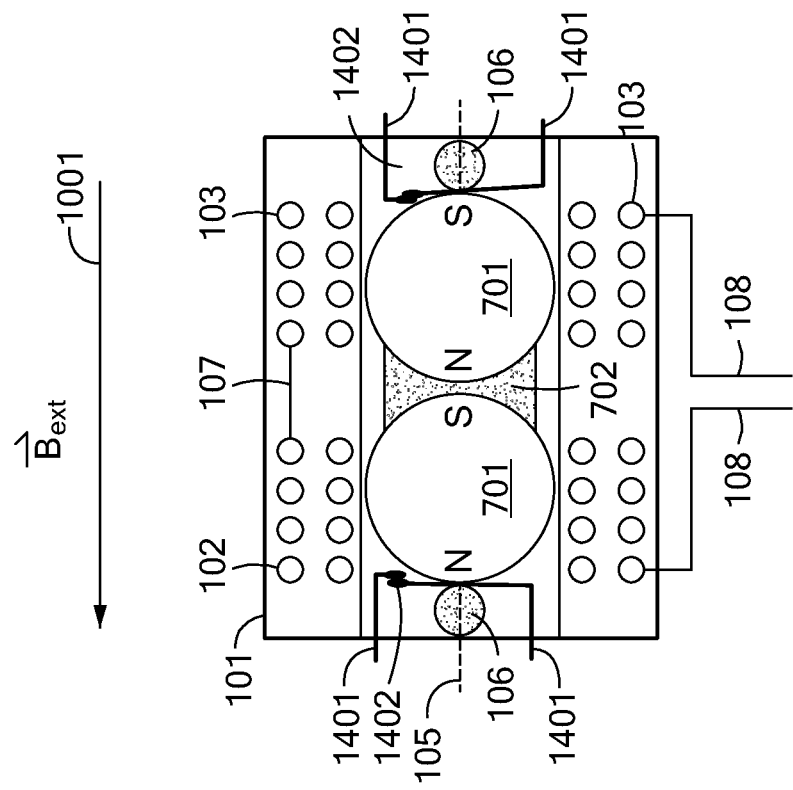
FIG. 14 schematically shows the electro-magnetic transducer of FIG. 10 that additionally includes a switch that is in a closed position, in accordance with one embodiment of the invention.
Figure 15:
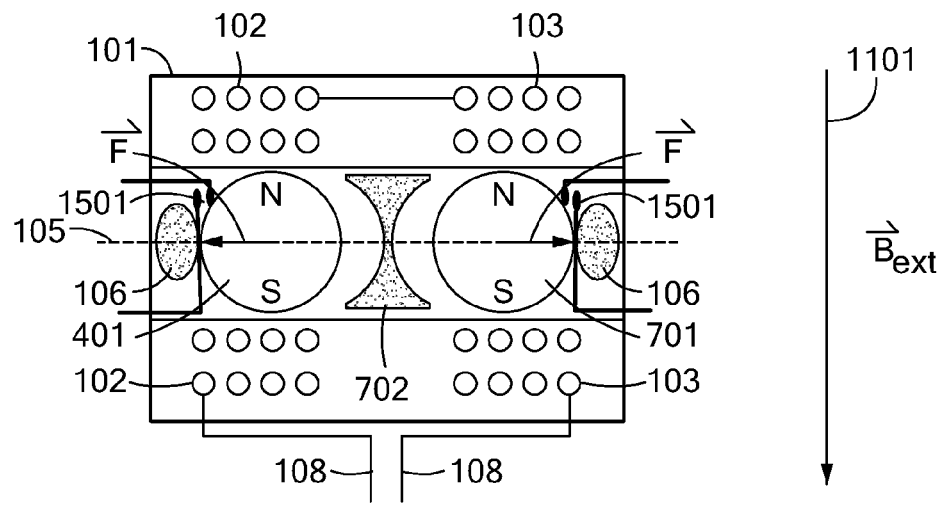
FIG. 15 schematically shows the electro-magnetic transducer of FIG. 11 that additionally includes a switch that is in an open position, in accordance with one embodiment of the invention.

The situation in which both magnets 704 and 705 are repelling each other (i.e., when a strong magnetic field perpendicular to the device's axis 105 is present) may be additionally exploited for a switching function. For example, FIGS. 14 and 15 illustrate the switch shown in FIGS. 10 and 11, respectively, having electrical connections 1401 and electrical spring contacts 1402 added, in accordance with an embodiment of the invention. In the absence of any external magnetic field or in the presence of a strong magnetic field parallel to the axis of symmetry of the device, as shown in FIG. 14, the spring contacts 1402 are closed. In the event of heavily vibrating magnets, the two electrical switches may temporarily open but at any time one of the two contacts is closed. In the presence of a strong magnetic field normal to the axis of symmetry of the device, as shown in FIG. 15, both spring contacts 1402 are open because the two spherical magnets are repelling.

Further embodiments may include more than two spherical magnets. Magnets of any shape (e.g. a cube) may be embedded into a sphere or a cylinder. Parts of low mechanical friction (e.g. Teflon®) and/or low magnetic reluctance may be placed between each two magnets. Such parts may have a shape that fits optimally between two spheres and may help to further reduce the torque exerted to the embodiment. In other embodiments the spherical magnets may be coated by a layer of low friction (e.g. Teflon®) or may be immersed in a lubrication material to minimize friction. Also, ball bearings instead of low-friction gliding elements may be placed between the spherical magnets.

With regard to the above-described electromagnetic transducers for translational vibrations, the vibrations of the magnet(s) may be transferred to the housing via biasing members 106. Such designs are called "floating mass transducers." In various embodiments, the biasing members are positioned between the vibrating magnet(s) and the housing so as to prevent the magnets from directly contacting the housing. As described above, the biasing members 106 may be used to define a resonance frequency, and/or to reduce friction between the magnet(s) and the interior surface of the housing that may cause distortion. The biasing members 106 are typically flexible and resilient, and may be made of, without limitation, silicone and/or a spring-like material.

Figure 12:
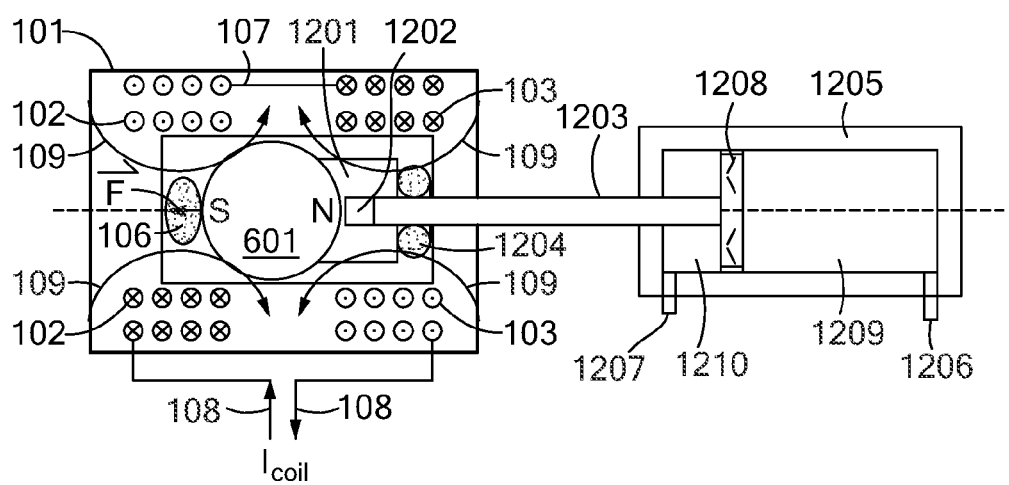
FIG. 12 schematically shows an electro-magnetic transducer acting as a mechanical stimulator, the transducer including a spherical magnet, a keeper, and a shaft, in accordance with one embodiment of the invention.

The vibrating magnets in the above-described embodiments may drive shafts and/or fluids (hydraulic drivers) instead of vibrating the housing, as shown, without limitation, in FIG. 12. FIG. 12 is a modification of the embodiment shown in FIG. 6, which includes one spherical magnet 601 and a keeper 1202

Similar to FIG. 6A, the keeper 1202 is held in place by a non-magnetic adapter 1201 (adapter 602 in FIG. 6A) which is connected to a shaft 1203 (note that alternatively, the non-magnetic adapter 1201 may not be needed if the keeper 1202 itself is shaped so as to maintain itself centered on the axis 105, and if the shaft 1203 is connected to keeper 1202). Due to the shaft 1203, biasing member 1204 may be shaped as a resilient torus. A current flow through the coils 102 and 103 can push can or pull the shaft (1203). The shaft 1203 may have, at one end, a piston 1208. The piston 1208 may, without limitation, separate fluid chambers 1209 and 1210 in a container (1205), the container having a fluid inlet 1206 and a fluid outlet 1207. If the piston 1208 is developed as a valve (e.g. allowing to pass fluids only from chamber 1209 to chamber 1210), vibrations of the magnet can pump a fluid, which may be a gas. Alternatively, fluctuations in fluid/gas pressure between the two chambers 1209 and 1210, which are separated by the piston, can induce voltages in the coils, such that the transducer acts as a sensor.

Figure 13:
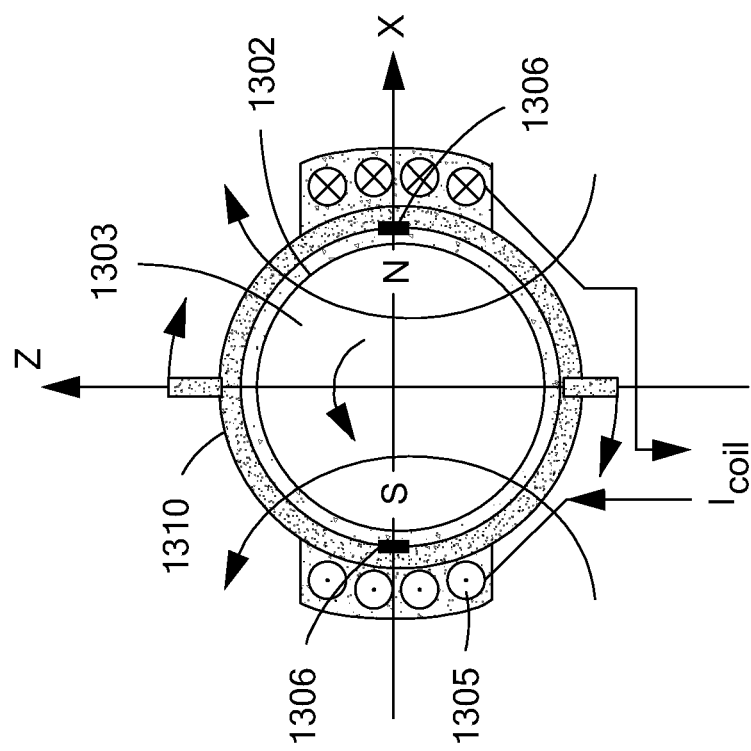
FIG. 13 schematically shows an electro-magnetic transducer acting as a rotational mechanical stimulator, in accordance with one embodiment of the invention.

In accordance with another embodiment of the invention, a transducer 1300 includes a housing 1310 with a coil 1305 and a spherical magnet 1303, as shown in FIG. 13. The spherical magnet 1303 is mechanically free to turn into any direction. In the absence of any external magnetic field and when there is no current flow through the coil 1305, the spherical magnet 1303 is self-aligning (i.e. has a magnetically stable orientation) because of one or more keepers 1306 and 1307 which are fixed in the housing 1310 and which attract the magnetic poles of the sphere 1303. An alternating current flowing through the coil 1305 generates a magnetic field which exerts a torque to the spherical magnet 1303. Due to the moment of inertia, the sphere 1303 cannot respond (i.e. rotate) fast enough, and a torque in opposite direction is exerted also on the coil 1305 which is fixed relative to the housing 1310. Therefore, an alternating current flow through the coil 1305 causes a rotational vibration of the housing 1310 which may be alternatively employed instead of a translational vibrating electro-magnetic transducer. This embodiment of an electro-magnetic transducer (called "rotating mass transducer") is free of torque and cannot be demagnetized in the presence of a strong external magnetic field of any direction and orientation, like those occurring, without limitation, in a Magnetic Resonance Imaging (MRI) environment.

The above-described electro-magnetic transducers can be used as a driver/stimulator by applying a current to said coil(s). In various embodiments, the coil(s) may be attached to leads that are attached to further circuit elements, which may include, without limitation, a processor or other control elements as known in the art. The electro-transducers may be used, for example, to improve hearing of the subject. This may include, without limitation, securing the housing of the electro-magnetic transducer to an ossicle in the middle ear.

Figure 9:
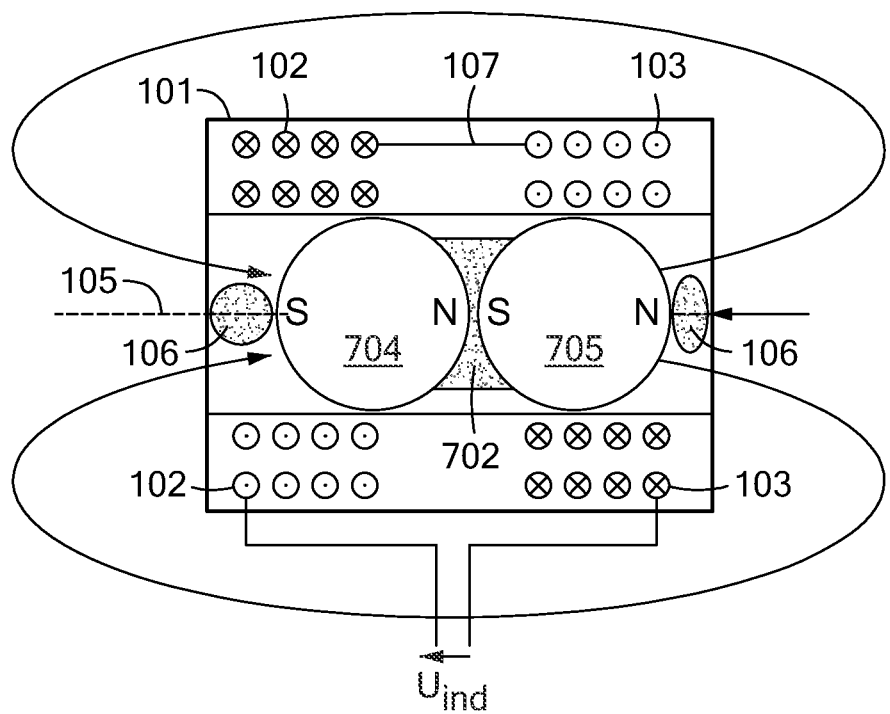
FIG. 9 schematically shows the embodiment of FIG. 7 acting as motion sensor, in accordance with one embodiment of the invention.

In other embodiments, the above-described electro-magnetic transducers may be employed as a sensor when operated in reverse mode. For example, FIG. 9 shows the embodiment of FIG. 7 acting as a sensor. Vibrations (or, in case of the Rotating Mass Transducer, rotations) generate induction of voltages in the coil(s). Such a sensor may be used, without limitation, in auditory implants to detect the motion of the ossicles, either as a "microphone" in the middle ear or to detect the stapedius reflex.

In various embodiments of the invention, electro-magnetic transducers for translational motion containing (spherical) magnets that can mechanically rotate, as described above, may be also employed as electro-magnetic transducers with adjustable polarity. The mechanical response (movement direction of the magnets) to a certain current input into the coil depends on the actual orientation of the magnetic moment(s) of the magnet(s), which may be altered by applying a strong anti-parallel external magnetic field.

The above-described embodiments of electro-magnetic transducers with magnets that are mechanically free to turn are free of torque during the presence of a strong external magnetic field of any orientation. A small torque may momentarily be exerted during a change of the orientation of the external magnetic field due to friction among the turning magnet(s) and also between the magnet(s) and the housing. Therefore, measures to reduce friction may be used to avoid these small amounts of torque due to friction. These measures include, without limitation, coating the magnets and/or inner surfaces of the housing with Teflon® or similar materials, or using various lubricants known in the art.

Furthermore, embodiments of electro-magnetic transducers with two or more differential coils, that are winded in different orientations, can be designed, as described above in connection with FIG. 4, such that the total voltage induced in the transducer coils resulting from RF pulses is substantially zero. This can be particularly advantageous for MRI applications.

Figure 16:
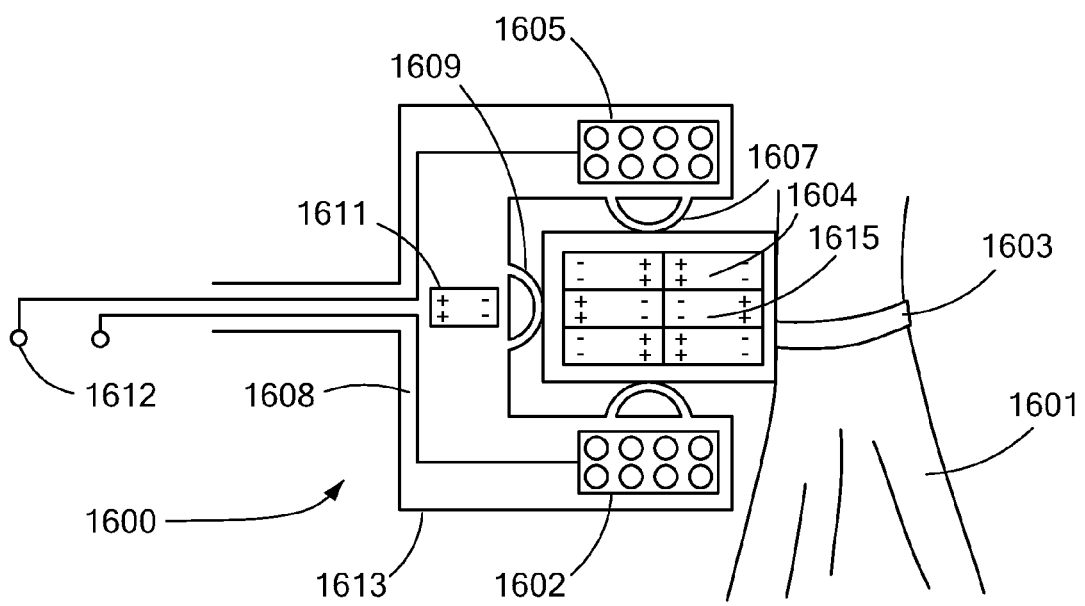
FIG. 16 schematically shows an electromagnetic transducer assembly that may be affixed to the stapedius of an ear, in accordance with one embodiment of the invention.

FIG. 16 schematically shows an electromagnetic transducer assembly 1600 that may be affixed to a structure. The structure may be, for example, the stapedius 1601 of an ear, or other vibrating structures associated, without limitation, to the ear or other tissue. In other embodiments, the structure may be a non-biological structure associated with vibration.

The electromagnetic transducer assembly 1600 illustratively includes a first component 1615 that includes at least one magnet 1604. The first component 1615 may attach to the structure, such as the stapedius, via a first attachment mechanism 1603.

The first component 1615 is removably coupled to a coil assembly 1613 via a second attachment mechanism that may include, without limitation, retaining mechanisms 1607 and 1609, for holding the first component 1615. The coil assembly 1613 may include a housing 1608 for housing at least one coil 1602 and 1605. The housing 1608 may be made of a biocompatible material known in the art, such as titanium. Various magnet(s) 1611 may be used to hold the coil 1602/1603 in a proper position within housing 1608.

The coil 1602 and 1605 produces a signal representative of the vibration of the at least one magnet 1604 associated with the first component 1615. An output port 1612 may extend from the coil assembly 1613, and may be used, for example, to interface with additional circuitry, such as a computer or other monitoring apparatus used to store and/or analyze the signal.

FIGS. 17(a) and 17(b) schematically show a first component 1701 of the electromagnetic transducer, in accordance with one embodiment of the invention. The first component 1701 includes a housing 1702 that, similar to the housing 1608 of coil assembly 1613, may be made of a biocompatible material, such as titanium. The housing 1702 advantageously may have a plurality of magnets 1703 and 1705 arranged in anti-parallel configuration. For example, the first component 1701 may include two cylindrical magnets 1705 and four ring magnets 1703 arranged in anti-parallel configuration, as shown in FIG. 17(b). Other magnetic configurations may be used, such as one or more spherical magnets, as described in above embodiments, that reduce the effects of an external magnetic field. In various embodiments, the first component 1701 may include at least one magnet capable of turning in any direction within the housing 1702, with movement of each magnet substantially restricted to movement along a single axis, and wherein vibration of the housing causes vibration of the at least one magnet.

FIG. 18 schematically shows portions of a coil assembly 1801 of the electromagnetic transducer, in accordance with an embodiment of the invention. As described above, the coil assembly 1801 may include retaining mechanisms 1803 for properly positioning and/or retaining the first component within the coil assembly 1801. The retaining mechanisms 1803 may be, without limitation, springs or other biasing mechanisms, that may provide a desired mechanical resonance associated with the first component 1701 and associated magnet, for example, below 100 Hz. Note that biasing elements may also be included within the housing of the first component that bias movement of magnet(s) within the first component 1701, without, or in combination with, any biasing mechanism associated with retaining mechanisms 1803, similar to above-described transducers. The housing of the first component may include one or more indentations or stops to assist in aligning and/or retainment.

In response to the first component/magnet vibrating based on, without limitation, movement of the stapedius, a coil 1805 positioned within coil assembly 1801 provides a current. A magnet 1807 may be utilized to properly position the coil 1805 within a housing (not shown in FIG. 18).

Figure 20:
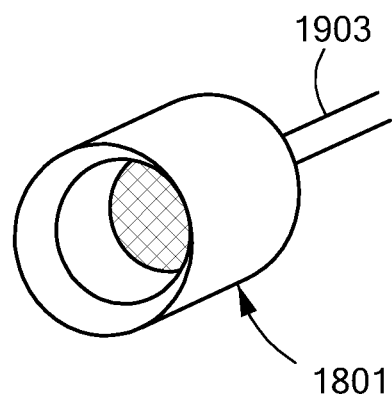
Figure 21:
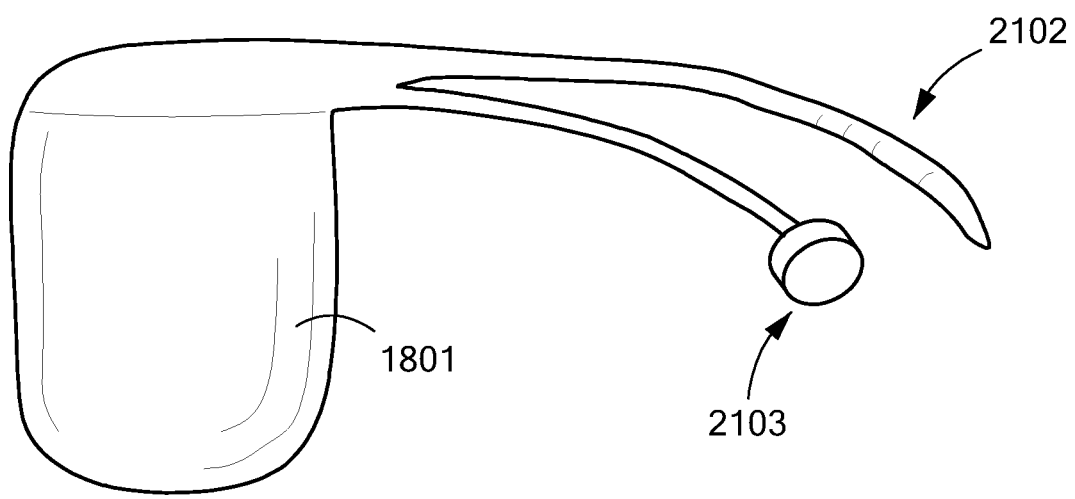
FIG. 21 shows a lead associated with the coil assembly that includes a female and a male electrodes for interfacing/connecting with additional circuitry, in accordance with one embodiment of the invention.

FIGS. 19 and 20 show varying views of the coil 1805, in accordance with one embodiment of the invention. Illustratively, the coil 1805 is of a female design, into which the first component is inserted. The coil 1801 includes a lead 1903 for outputting current generated by coil. Note that in various embodiments, current may be input onto the lead 1903 so as to cause current to flow in the coil 1801, causing the magnet to vibrate. As shown in FIG. 21, the lead may have female 2103 or male electrodes 2102 for interfacing/connecting with additional circuitry.

Figure 22A:
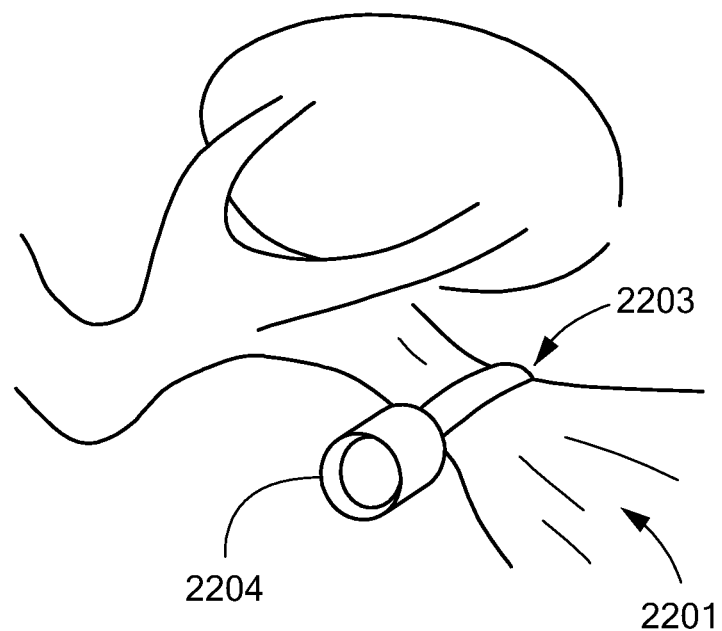
FIG. 22(a) shows a first component installed on the stapedius tendon, in accordance with one embodiment of the invention.

FIG. 22(a) shows the first component 2204 installed on the stapedius tendon 2201, in accordance with one embodiment of the invention. The first component 2204 includes a first attachment mechanism 2203 that is used by a surgeon to secure the first component 2204 to the stapedius tendon. The first attachment mechanism 2203 may be any one of various fasteners known in the art, such as, illustratively, a zip or wire tie, or a quick draw.

Figure 22B:
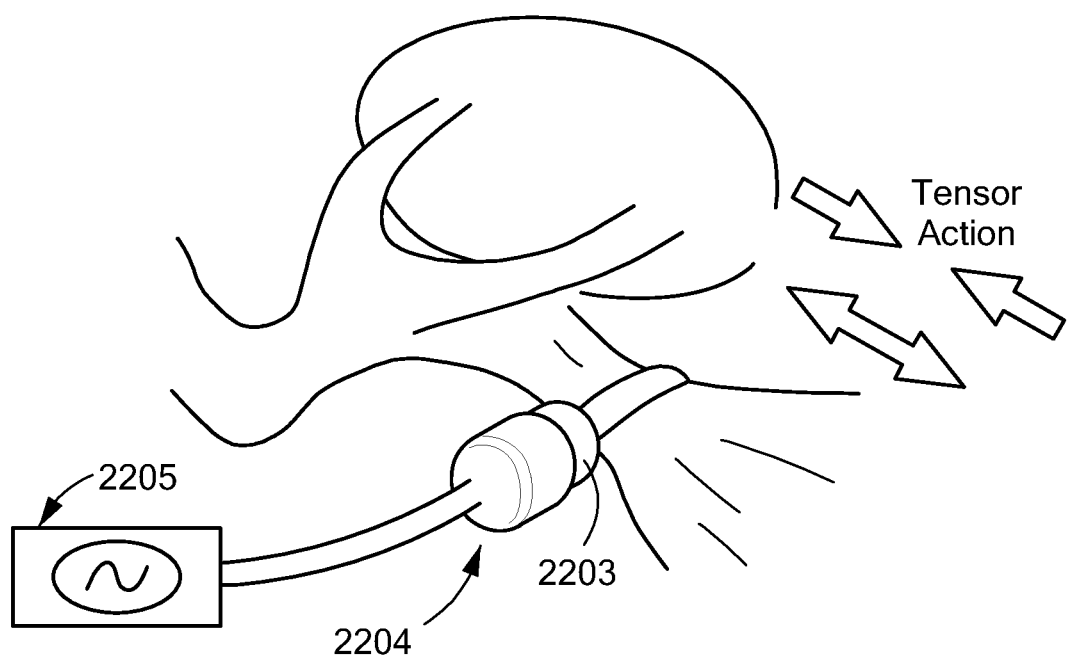
FIG. 22(b) shows a coil assembly attached the first component of FIG. 22(a) by inserting, the male shaped first component into the female shaped coil assembly, in accordance with one embodiment of the invention.

As shown in FIG. 22(b), a surgeon may then attach coil assembly 2204 to the first component 2203 by inserting, for example, the male shaped first component 2204 into the female shaped coil assembly 2204, in accordance with one embodiment of the invention. As the stapedius tendon fires and contracts, the magnet of the first component 2203 vibrates. This vibration causes a current in the coil associated with coil assembly 2204, that is transferred via leads to additional circuitry 2205, whereupon it may be, without limitation, monitored, read, stored and/or analyzed.

The signal produced by the electro-magnetic transducer assembly may be used, without limitation, to program/fit a hearing implant. For example, the tensing of the stapedius muscle triggered as a result of high sound pressures, also referred to as the stapedius reflex, may be used for setting and/or calibrating a cochlear implant, because the sound energy perceived by a patient may be concluded from the measured stapedius reflex. This testing may be particularly advantageous when dealing with very young patients with hearing implants/devices who cannot express their perception with verbal feedback, Such testing may be used, without limitation, over a period of weeks, to adjust stimulation amplitude of the implant/device.

The easily removed coil assembly of the electro-magnetic transducer is particularly advantageous when testing over a period of time is desired. After initial installation of the first component onto the desired vibrating structure, the coil assembly may be attached, and subsequently removed, any number of times, without removing the first component. That the magnet associated with the first component minimizes interactions with an external magnetic field, such as an applied external MRI magnetic field, as described above in various embodiments, advantageously results in reduced torque and/or demagnetization associated with the first component.

Although various exemplary embodiments of the invention have been disclosed, it should be apparent to those skilled in the art that various changes and modifications can be made that will achieve some of the advantages of the invention without departing from the true scope of the invention. These and other obvious modifications are intended to be covered by the appended claims.

What is claimed is:

1. A method for measuring a vibration of a structure associated with an ear of a patient, the method comprising:

attaching a first component to the structure, the first component including a biocompatible housing, at least one magnet enclosed within the housing;

attaching a coil assembly to the first component, the coil assembly including a biocompatible coil housing, at least one coil enclosed within the coil housing, the at least one coil for producing a signal representative of the vibration of the at least one magnet;

providing the signal to an output port of the coil assembly; and removing the coil assembly from the first component, leaving the first component attached to the structure.

2. The method according to claim 1, wherein the structure is a stapedius of the patient, the method including measuring a stapedius reflex of the patient.

3. The method according to claim 1, wherein the at least one magnet includes a plurality of magnets arranged in an anti-parallel configuration.

4. The method according to claim 1, wherein each magnet is capable of turning in any direction within the housing, wherein translational movement of each magnet is substantially restricted to movement along a single axis, and wherein vibration of the housing causes vibration of the at least one magnet.

5. The method according to claim 4, wherein the at least one magnet is substantially spherical.

6. The method according to claim 1, wherein the housing is male shaped, and the coil housing is female shaped housing, such that attaching the coil assembly to the first component includes inserting the male shaped housing into the female shaped coil housing.

7. The method according to claim 1, further comprising damping vibration of the at least one magnet.

8. The method according to claim 1, further comprising:
   programming a hearing implant based, at least in part, on the signal.

* * * * *